United States Patent [19]
Vander Meer et al.

[11] Patent Number: 5,897,859
[45] Date of Patent: Apr. 27, 1999

[54] ATTRACTANT FOR SOCIAL PEST INSECTS

[75] Inventors: Robert K Vander Meer; Clifford S Lofgren, both of Gainesville, Fla.

[73] Assignee: The United States of America as represented by the Secretary of Agriculture, Washington, D.C., DC

[21] Appl. No.: 08/906,091

[22] Filed: Aug. 5, 1997

[51] Int. Cl.$^6$ .................................................. A01N 25/00
[52] U.S. Cl. ............................................................ 424/84
[58] Field of Search ................................................ 424/84

[56] References Cited

U.S. PATENT DOCUMENTS 5,198,467  3/1993  Milks ........................................ 514/553

OTHER PUBLICATIONS

Pierce et al., "Attraction of *Oryzaephilus surinamensis* (L.) and *Oryzaephilus mercator* (Fauvel) (Coleoptera:Cucujidae) to some Common Volatiles of Food", *Journ. Of Chem. Ecol.*, vol. 16, No. 2, pp. 465–475, 1990.

Wassgren et al., "Pheromone related Compounds in Pupal and Adult Female Pine Sawflies, *Neodiprion Sertifer*, of Different Age and In Different Parts of the Body", *Journal of Insect Physiology*, vol. 38, No. 11, pp. 885–893, 1992.

Buttery et al., "Volatile Components of Alfalfa Leaf–Cutter Bee Cells", *Journ. Agric. Food Chem.*, vol. 29, pp. 955–958, 1981.

Tsuboi et al., "Highly Stereocontrolled Synthesis of (2E, 4Z)–Dienoic Esters with Alumina Catalyst. Its Application to Total Synthesis of Flavor Components and Insect Peromones", *Journal Org. Chem.*, vol. 47, pp. 4478–4482, 1982.

Banks et al., "Techniques for Collecting, Rearing, and Handling Imported Fire Ants", U.S. Dept. Of Agriculture, AAT–S–21/Apr. 1981.

Snyder et al., "Capillary Gas Chromatographic Analyses of Headspace Volatiles from Vegetable Oils", *JAOCS*, vol. 62, No. 12, pp. 1675–1679, Dec. 1985.

Miller et al., "Quantification of Carbonyl Compounds in Oxidized Low–Linolenate, High–Stearate and Common Soybean Oils", *JAOCS*, vol. 65, No. 8, pp. 1328–1333, Aug. 1988.

Snyder et al., "Comparison of Gas Chromatographic Methods for Volatile Lipid Oxidation Compounds in Soybean Oil", *JAOCS*, vol. 65, No. 10, pp. 1617–1620, Oct. 1988.

*Primary Examiner*—Amelia Owens
*Attorney, Agent, or Firm*—M. Howard Silverstein; John D. Fado; Gail E. Poulos

[57] ABSTRACT

An attractant for social pest insects has been discovered and isolated from soybean oil. This attractant is also found in canola oil. This attractant increases the effectiveness of baits and/or traps in the control of social pest insects.

9 Claims, 13 Drawing Sheets

ATTRACTANT FOR SOCIAL PEST INSECTS

BACKGROUND OF THE INVENTION

1. Field of the Invention

The present invention relates to an attractant for use in bait compositions and/or traps for social insects, particularly ants and more particularly fire ants. It also relates to the use of these compositions to control social insects.

2. Description of the Related Art

Attractants for insect control are used to lure insects to a toxicant and/or trap. They also can be used to identify the presence, distribution and population of an insect. Most commercially available baits for pest social insect control use a vegetable oil, such as soybean oil, or a sugar which act as phagostimulants in the baits. The oil is also the solvent for the active ingredient which is usually a toxicant. The solution is then absorbed onto an inert carrier, typically pre-gel defatted corn grits. The formulation can then be spread effectively to allow foraging insects to harvest the grits, taking them and the active ingredient into the nest. In the nest the liquid is sucked out of the grits and distributed to other colony members including the queen. The toxic baits take advantage of social insect foraging and food distribution systems to direct the toxicant to the entire colony. Thus, smaller quantities of insecticide are used then would be required for the inundation of colonies with, for example, insecticide emulsions (drenches). Thus, an effective attractant will facilitate the discovery and distribution of an active ingredient to an entire colony of social pest insects.

Control of social insects such as ants, yellow jacket wasps, other pest wasps and termites has long been a problem. Various species of ants pose significant problems for man from both an agricultural and a health care point of view. Leaf-cutting ant species can defoliate a citrus tree overnight. Argentine ants endanger crops by domesticating and protecting other pest insects such as aphids and scale. Fire ants are particularly destructive by stinging humans and livestock, feeding on germinating seeds and crop seedlings thereby reducing yields, damaging electrical equipment and damaging farm machinery which strike the ants' mounds.

Requirements for an effective pesticide formulation for the control of pest social insect species, such as ants, are very stringent because the reproductive forms (queens) of social insects are buffered from the effects of insecticides by a large worker force and their often closed nest structure. Thus, control of social insect pests is inherently different from control of non-social insects. For example, a mature fire ant colony may contain 250,000 sterile workers and a single queen. Only 10 percent of the workers are on the surface foraging for food. Insecticide treatment with a fast acting insecticide will not affect the 90% of the workers in the nest or the queen and the total effect is negligible. In fact, 95% of the workers can be killed, but if the queen is unaffected, the colony will come back. Thus, an effective social insect toxicant must exhibit delayed toxicity, not repel the insects and be effective over a range of concentrations. Repellency can reduce or negate the effectiveness of a toxicant because the insects will avoid a treated bait. A bait must be of a form that is transferable either by carrying it back to the nest or by trophallaxis and the toxicity must be delayed because foraging worker insects constitute only a small percentage of the total colony and must survive long enough to pass the toxicant onto the main colony population, especially the queen(s).

Identification of attractants is important in the development of integrated pest control programs. Most commercially available baits are formulated with either a vegetable oil or a sugar. U.S. Pat. No. 5,104,658 to Hagarty discloses an insecticidal bait composition which is effective against ants, centipedes, earwigs, firebrats, German cockroaches, harvestmen, millipedes, sowbugs, spiders and ticks. This composition includes the sugar maltose, pulverized cereal, animal or vegetable oils as the phagostimulant.

U.S. Pat. No. 4,985,413 to Kohama et al discloses a bait composition that is effective against a wide range of harmful insects such as cockroaches, pillbug, beetles, and ants including *Monomorium pharaonis, Monomorium niponense, Lasius fuliginosus* and *Formica japonica*. The composition includes crystalline cellulose, vegetable oils such as soybean oil, rapeseed oil, sesame oil, wheat germ oil, etc.; crop product powders such as potato starch, sweet potato starch, corn starch, wheat flour, rice powder, corn powder, etc.; a saccharide such as sugar, glucose, D-fructose, lactose, black sugar, brown sugar, soft brown sugar, etc.; and an insecticide.

There are many reports on volatiles that contain attractive chemicals for insects. Tsuboi et al (J. Org. Chem., Volume 47, 4478–4482, 1982) report that certain insect pheromones have conjugated E,Z-diene systems. They also disclose that(2E,4Z)-Dienoic esters are important compounds having utility as aroma agents for food, drinks and tobacco. The reference is directed to synthetic methods for 2E,4Z-Dienoic esters and is silent on the use of these compounds as attractants in baits for the control of social pest insects. Buttery et al report that (E,Z)- 2,4-heptadienal is a component in the volatile oil extracted from leaf-cutter bee cells obtained from a number of different natural nesting sites. However, the reference is silent as to any activity of this component of the extracted volatile oil. Wassgren et al (J. Insect Physiol., Volume 38 (11), 885–893, 1992) report the presence of (E,E)-2,4-heptadienal and (E,E)-2,4-decadienal in whole body extracts of female pine sawflies but the reference states that the function of these two compounds is unknown and notes that these two components have a structural relationship to (E,Z)-2,4-decadenoate which is a pheromone component of the spruce engraver beetle. Pierce et al (Journal of Chemical Ecology, Volume 16 (2), 465–475, 1990) disclose that two olefinic oat volatiles, 2(E),4(E)-heptadienal and 3(E),5(E)-octadien-2-ol were attractive at 0.1–10 $\mu$g for the beetle *O. surinamensis* (sawtoothed grain beetle) and *O. mercator* (merchant grain beetle). However, the reference fails to specifically mention the use of these compounds in baits.

There remains a need in the art for highly effective attractant formulations for the control of social pest insects. The present invention provides an attractant for use in baits and/or traps for the control of social pest insects that is different from related art attractants.

SUMMARY OF THE INVENTION

It is therefore, an object of the present invention to provide an attractant for the control of pest arthropods.

Another object of the present invention is to provide an attractant composition in a matrix which further includes a toxicant and a phagostimulant.

Still another object of the present invention is to provide 2,4-heptadienal as an attractant in a bait formulation also containing a toxicant and a phagostimulant.

Another object of the present invention is to provide a method for controlling pest social insects that includes 2,4-heptadienal as an attractant in a bait formulation.

A still further object of the present invention is to provide an attractant in a trapping system for control and/or monitoring of pest social insects.

Further objects and advantages of the present invention will be apparent from the following detailed description.

BRIEF DESCRIPTION OF THE DRAWINGS

FIG. 4a is a total ion chromatogram. The DB-225 column was programmed as in FIGS. 2 and 3a.

DETAILED DESCRIPTION OF THE INVENTION

Figure 1:
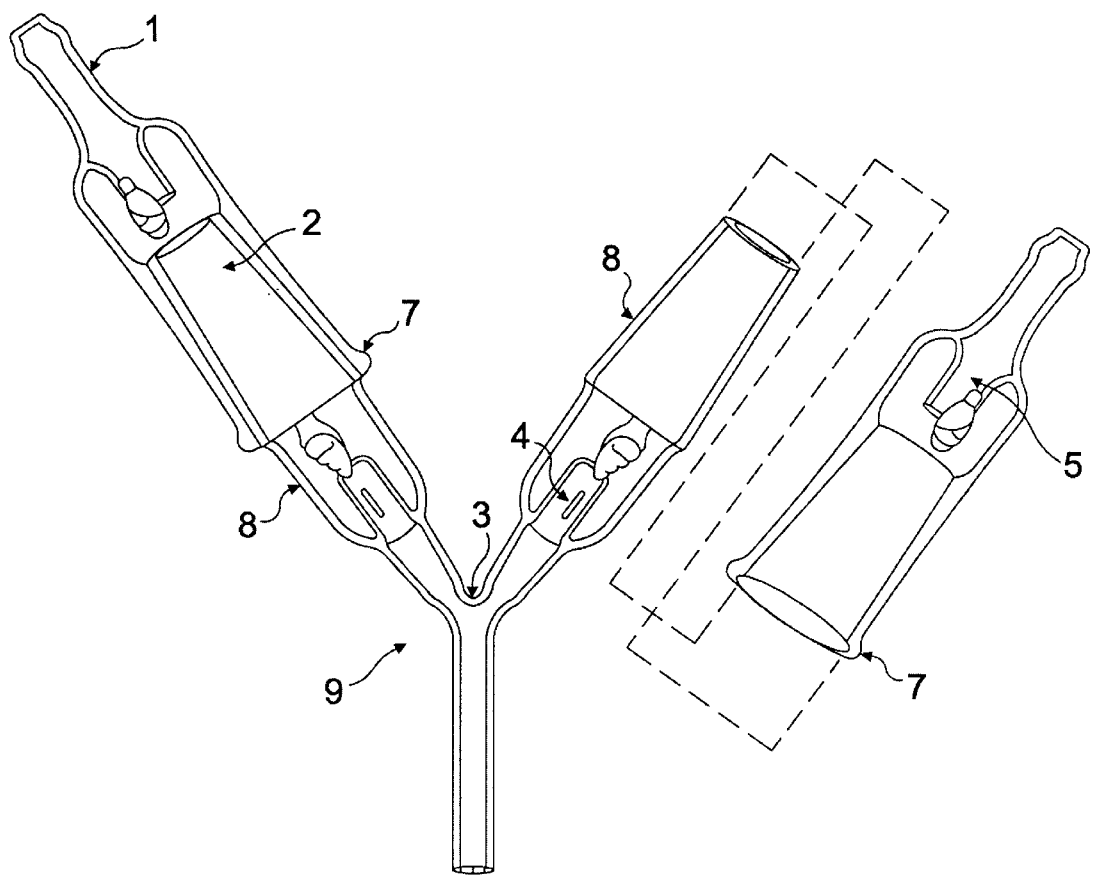
FIG. 1 is a drawing of an olfactometer showing air inlet tube 1, sample chambers 2, baffle 3, ring seal tubes front 4 and rear 5, entrance stem 6, ring 7, arms 8 and y-tube 9.

The fire ant, *Solenopsis invicta,* is used as a model system. The concept is applicable to the control of other pest ants and other pest social insects such as wasps and termites which have well developed foraging/recruitment mechanisms. Social insect pests are treated in accordance with the invention by dispensing the attractant-containing formulation in any suitable way in the vicinity of nests, in urban or rural areas, or anywhere pest social insects are a problem.

Two species of fire ants were accidently imported into the United States. The black imported fire ant, *Solenopsis richteri,* was introduced in the early 1900's to the Mobile Alabama area. A red form of fire ant was introduced to the same area in the 1930's. The red imported fire ant was subsequently named *Solenopsis invicta.* The red imported fire ant dominated *S. richteri* and the native ant species of the area. Spread of *S. invicta* occurs at about 2–6 miles per year through mating flights. However, they spread much more quickly by infesting nursery stock which was then transported throughout the south and southeast. With these population enclaves in place the red imported fire ant filled in the gaps until now about 55 years later they currently inhabit over 150 million hectares in Puerto Rico and twelve southern states from Texas to Virginia (NC, SC, GA, AL, MS, FL, LA, TX, OK, AR, TN, VA). It has also been reported in California, Arizona, New Mexico, and Maryland, but these infestations have been eradicated. Freezing winter temperatures have slowed its northward expansion, as have arid conditions in western Texas. Eventually, *S. invicta* is expected to expand its range southward into Mexico and westward along irrigated areas into California. Mature IFA colonies may contain 250,000 workers and reach infestation rates of over 130 mounds per hectare. With proliferation of the polygyne form (multi-queen colonies) of the IFA in the Southern states in the last decade, it is not uncommon to find millions of fire ants per acre existing in one super colony with hundreds of small mounds. Control is difficult because all queens must be killed. The IFA literally destroy all other ground inhabiting arthropods and other small animals. Since IFA are highly aggressive when their nests are disturbed, which often results in painful stings to humans and their pets, there are more reports of personal injury to people and pets where the polygyne form of IFA are present. Approximately 30% of the people in the infested areas are stung each year and about 1% of the population may develop hypersensitivity to the ant's venom and require some type of medical care, which means that 75,000 persons per year may require the aid of a physician.

With the spread of the fire ant came an increasing awareness that they cause numerous problems ranging from medically-related concerns associated with their stings, to agronomic losses because of interference with farming operations, destruction of crops and injury or death of young animals. The extent of these problems on farms was suppressed because of the wide scale use of residual chlorinated hydrocarbon insecticides from 1950 to 1970. Because of environmental concerns, registrations for these highly effective insecticides were canceled with the result that populations of the IFA on farms increased dramatically. In a 1987 survey of soybean fields in 6 states, it was revealed that there was an average mound density of 50 per acre. The potential impact of these general infestations is immense when it is considered that published data show potential losses of 5–6 bushels of soybeans per acre associated with the ant densities cited above.

Similar problems have been shown to occur in other agronomic crops in the South. IFA polygyne densities as high as 200 mounds per acre have been recorded in young citrus groves. Extensive ant feeding on the bark and sap of the trees (1 to 4 years old) has caused up to 15% of them to be killed. Based upon estimated costs published by the University of Florida citrus specialists, replacement of these trees would amount to about $1000 per acre. IFA have also been associated with huge increases in aphid and scale populations in pecan trees as a result of their predation on parasites of these pests.

Because of the potential public health, agricultural and environmental problems associated with the IFA, it is imperative that their spread be prevented. Withdrawal of EPA regulations of MIREX® in the late 1970's for treatment of quarantined articles complicated the control of the spread of IFA. Long range spread of IFA is probably associated with transport of entire colonies. Since small colonies require high moisture conditions and prefer nesting in soil, it is most likely that soil transport, such as that associated with live plants and sod, is a major method of spread. New infestations of IFA are usually found by visual inspection after the colonies are large enough to build obvious mounds. By this time, mating flights from these colonies have taken place and the eradication of even small infestations becomes difficult and expensive.

The detection of incipient infestations is complicated by the fact that they either do not build mounds, or if they do, the mounds are very small. The workers do not fly, so survey traps based on flight are not feasible. Thus, the only practical approach is to look for infestations after mounds are built or to develop attractant compositions for baits and/or traps for the foraging workers. The use of an attractant composition is practical since IFA have an effective foraging system which involve a series of underground tunnels with exit holes to the surface every 15 to 20 inches. It has been established that the furtherest distance that ants in a mature colony have to travel to reach an exit hole ranged from 10 to 16 inches. However, the ants foraging area is three dimensional and very complex. An attractant composition would increase the probability of foraging ants finding bait particles.

IFA workers are recruited readily to a variety of foods and food baits once the food is discovered. Like other vegetable oils, soybean oil is a good phagostimulant for fire ants. Surprisingly, once refined soy bean oil (ORSBO) also contains a volatile attractant that has been isolated and identified. The attractant can be collected readily by bubbling nitrogen gas through soybean oil heated to about 50–55° C. and collecting the volatiles in a Dry Ice trap. Olfactometer tests have confirmed that the volatiles collected are as attractive as soybean oil. Tests have also shown that when the attractant is added to vegetable oils that are not attractive but have phagostimulant properties, such as peanut and olive oils, these oils become attractive. Gas chromatograph (GC) and mass spectrometry (MS) work was used to determine the chemical composition of the attractive components in the soybean oil volatile mixture. Two bioassays were used to determine the location of the attractive components in the separated volatiles. In the first method, the complex volatile mixture was separated on a GC using a 10:1 splitter at the effluent end of the GC column. One part went to the detector and ten parts were directed to a capillary collection tube cooled with dry ice. Effluent fractions were collected in the tubes and eluted into vials with hexane. These samples were evaluated in an olfactometer bioassay. In the second method, the GC effluent was split as described above with one part going to the detector and ten parts directed via a short length of TEFLON tubing to a small tray containing a fire ant sub-colony (worker ant activity bioassay). The column effluent was aimed at a worker food trail and the behavior of the ants was monitored. The ants exhibited excitement whenever an active compound came through the column. Comparison of the time of activity and the time of peak elution (via the detector) showed which peaks were behaviorly active. The two methods gave consensus on the location of the active compounds in the gas chromatogram. GC/MS identified components in that region of the chromatogram were trans,trans-2,4-heptadienal and trans,cis-2,4-heptadienal. Trans,trans-2,4-heptadienal is commercially available (Aldrich Chemical Company). Side-by-side concentration/activity studies of soybean oil volatiles and trans,trans-2,4-heptadienal showed that the shape of the two concentration curves were similar. Amplitude of the trans,trans-2,4-heptadienal curve was not as great as that of the equivalent concentration of soybean oil volatiles. This indicates that trans,trans-2,4-heptadienal alone is not responsible for all the attractiveness of once refined soybean oil to fire ants. It is suspected that equivalent amounts of the two heptadienal isomers present in soybean oil will give full activity.

The term "bait" is understood by those skilled in the art to be any substance that will entice an insect to ingest an active ingredient, such as for example a toxicant, an insect growth regulator, etc.; and/or enter a trap and includes a phagostimulant, an active ingredient, a suitable carrier and/or a trap. Baits use once refined soybean oil (ORSBO) only as a phagostimulant and a solvent for the active ingredient. However, ORSBO is no longer available. The more refined soybean oil which is available does not have attractant properties. A phagostimulant is any substance that will entice the insect to ingest the toxicant. Suitable phagostimulants include edible oils and fats, vegetable seed meals, meal by-products such as blood, fish meal, syrups, honey, sucrose and other sugars, peanut butter, cereals, amino acids, proteins, etc. See U.S. Pat. No. 3,220,921 which is herein incorporated by reference. Preferred phagostimulants for ants are mixtures of edible oils, which are also solvents for toxicants.

The attractant, 2,4-heptadienal, can be used as trans,trans-2,4-heptadienal, trans,cis-2,4-heptadienal or as mixtures of the two. The attractant is used in amounts effective to attract pest social insects to a bait and/or trap. Preferred amounts are in the range of about 0.001% to about 2% (weight:weight). A more preferred range is about 0.003% to about 0.03% (weight:weight).

Nonlimiting examples of suitable carriers include, for example, corncob grits, pregel defatted corn grits (PDCG), diatomaceous earth, alumina, silica, clays, other suitable inorganic oxides, polymers, extruded corn, powdered carbohydrates such as corn starch, dextrans and cellulose; and the like. Preferred carriers include pregel defatted corn grits.

The active ingredient can be any substance which kills or inhibits the reproductive capabilities of the pest social insect. Active ingredients suitable for use with the attractant composition of the present invention include for example, organophosphates, carbamates, arsenicals, pyrethroids, insect growth regulators, boric acid, silica gel, borate, etc. See for example U.S. Pat. No. 5,104,658, which is herein incorporated by reference. See also, for example, U.S. Pat. No. 5,177,107; herein incorporated by reference, for other toxicants that are useful in the present invention. The active ingredient is in amounts effective for controlling pest social insects as long as it is not repellent to the targeted insect when it is incorporated into the attractant composition.

The attractant composition of the present invention can be combined with the carrier by any appropriate means. For example, a solid carrier can be soaked with the attractant composition resulting in a solution or suspension wherein the attractant is deposited or impregnated into said carrier material. The treated carrier material can then be applied by spraying the area or object to be treated; by broadcasting, by applying to cracks and crevices, and by applying a gel; for example. The treated material may also be placed in a trap.

Each component of the bait and/or trap should be present in an effective amount. The expression "effective amount" is defined herein to mean that amount which is necessary to achieve the intended result of the component in question. For example, an effective amount of a toxicant is that level or concentration which will kill significantly more target insects when a bait is consumed than when an equivalent amount of bait is consumed without the toxicant present. Likewise, an effective amount of an attractant is that which will attract more target insects to a bait and/or trap than a control bait and/or trap without the attractant.

The following examples are presented to illustrate the invention. Control of social insects is illustrated using fire ants as a test model system. These examples are intended to further illustrate the invention and are not intended to limit the scope as defined by the claims.

EXAMPLE 1

The olfactometer bioassay uses an olfactometer (FIG. 1) which consists of two 24/40 ground glass joints each ring sealed to one of the arms 8 of about a 5 cm Y-tube 9 such that about 1 cm of each Y-tube arm 8 extends through the male half of one of the ground glass joints. About a 5 cm piece of about a 0.6 cm i.d. tubing 4,5 is ring-sealed into the female half of the ground glass joints. Baffle 3 at the center of the Y-tube 9 controls air streams and prevents premature mixing of the sample. It gives the ants a clearer choice. Baffle 3 also narrows the openings to the choice chambers to the minimum size required for passage of a major worker ant. A test sample (approximately 10 μl) and a solvent blank of approximately 10 μl are applied to two filter paper strips of approximately 0.3×2.5 cm Whatman No.1, air-dried and each placed in one of the choice chambers 2. Compressed air (breathing quality) is split into two streams and passed into the two choice chambers 2 through air inlet tubes 1. Each stream is regulated to about 0.2 liters/minute for a total effluent flow-rate of about 0.4 liters/minute. Approximately 50–70 ants from laboratory colonies are confined in about a 2.5 cm piece of about 0.9 cm i.d. TYGON tubing sealed at one end with wire gauze. The open end of the tubing is attached to the entrance stem 6 of the olfactometer. The initial choice of the first 20 ants that walk down entrance stem 6 and into one of arms 8 of Y-tube 9 is recorded. Ants that are not trapped in a choice chamber 2 and come back to the entrance stem are not counted if they make another choice. After each test, the olfactometer is rinsed with acetone and dried. Each test sample is retested with worker ants from the same colony but the choice chamber 2 in which the sample and control are placed is reversed. This procedure eliminates any bias inherent in the individual olfactometers. A complete replicate is the sum of the results from the two tests. Data are analyzed statistically using the chi-square test and comparisons between means are made with the Newman-Keuls' test. Table 1 below shows results with tests using fire ant Queen pheromone as the positive control, hexane as the negative control and different oils as the test sample. Note that $\bar{x}\% < 65$ or $X^2 < 3.6$ is not significantly attractive.

TABLE 1

Results of Olfactometer Bioassays
of the Queen Pheromone and Several Oils

| Sample | x̄ % | SE | N–K | $X^2$ |
|---|---|---|---|---|
| 1. Queen | 81.4 | 0.8 | A | 14.4 |
| 2. Soy Bean Oil | 72.0 | 2.0 | B | 8.1 |
| 3. Safflower Oil | 65.5 | 3.2 | BC | 3.6 |
| 4. Peanut Oil | 62.3 | 3.6 | CD | 2.5 |
| 5. Sesame Oil | 60.8 | 1.5 | CDE | 1.6 |
| 6. Hexane | 58.3 | 1.2 | CDEF | 0.9 |
| 7. Cod Liver Oil | 56.5 | 5.9 | DEF | 0.4 |
| 8. Mineral Oil | 54.8 | 2.0 | DEF | 0.4 |
| 9. Almond Oil | 54.5 | 3.3 | DEF | 0.4 |
| 10. Olive Oil | 53.5 | 2.6 | EF | 0.1 |
| 11. Walnut Oil | 52.0 | 1.8 | F | 0.1 |

The queen pheromone was significantly more attractive than any of the oils with 81.4% of ants attracted while soybean oil was the most attractive of the oils. Statistically, safflower oil was as attractive as soybean oil but it was not significantly more attractive than the blank hexane. The results of the olfactometer tests clearly show that soybean oil has attractive qualities.

EXAMPLE 2

The attractants from once refined soybean oil are isolated by bubbling nitrogen gas through soybean oil that has been heated to about 50° C. The volatiles are collected in a Dry Ice cold trap. The olfactometer bioassay was used to confirm that the volatiles are as attractive as soybean oil using the method described above in Example 1. About 10 μl of about a 10% hexane solution of soybean oil or soybean oil volatiles are used in each test. Volatiles were collected at three temperatures. Results are shown in Table 2.

TABLE 2

| Attractant | #Tests | Temp. ° C. | Mean % Response and Range |
|---|---|---|---|
| Soybean oil | 6 | — | 72.9 (62.5–80.0) |
| Volatiles | 4 | 26–28 | 55.0 (50.0–60.0) |
| Volatiles | 13 | 50–55 | 71.2 (47.5–80.0) |
| Volatiles | 4 | 95–105 | 45.0 (40.0–50.0) |

EXAMPLE 3

The identification of the component(s) in the soybean volatiles was accomplished combining gas chromatography, mass spectrometry and olfactometer bioassays (Example 1). Once refined soybean oil was placed in a gas dispersion bubbler. Nitrogen gas was passed through an activated coconut charcoal filter (6–14 mesh; Fisher Scientific Co., Fair Lawn, N.J.), then bubbled through the soybean oil. The nitrogen gas and soybean oil volatiles were carried through TEFLON tubing to the inlet side of a condenser finger from a mini-distillation apparatus. The condenser finger was immersed in a Dry-Ice acetone bath. Collections were made with the soybean oil heated in a mineral oil bath at about 26–28°, 50–55°, or 100° C., for durations lasting up to about six(6) hours. After each collection the condensed volatiles were removed by inserting a piece of TEFLON tubing to the bottom of the condenser finger, then the liquid was sucked into the tubing with a glass syringe. The collected volatiles were evaluated in the olfactometer bioassay. The most effective collection temperature was about 50–55° C. (See Table 2 above). Thus, subsequent collections were carried out at this temperature.

The trapped volatiles were extracted with approximately 150 μl of hexane (American Burdick and Jackson, Muskegan, Mich.) or n-dodecane (Aldrich Chemical Co., Milwaukee, Wis.) to remove the organic compounds from co-condensed water. These extracts were used in subsequent bioassays and chemical analyses.

For chemical analysis, the extract was analyzed by gas chromatography (GC) on a Varian 3700 gas chromatograph equipped with a flame ionization detector and the following column: J&W DB-225 (about 50% cyanopropylphenyl), approximately 15M, approximately 0.259 mm ID, approximately 0.25 μm film thickness. The following temperature programs were used: approximately 25° C. for about 10 minutes, then to approximately 185° C. at about 10°/minute, or approximately 32° C. to 185° C. at about 10°/minute. Data was analyzed on a Varian 402 Data Processor.

For mass spectra, electron impact (EI) spectra were acquired at about 70EV and chemical ionization (CI) spectra were obtained using methane as the reactant gas. The mass spectra were obtained on a Hewlett Packard 5988 GC/MS System connected to a HP 5890 gas chromatograph equipped with the column described above. The mass spectral data were acquired and processed with a HP 9000 Series 300 computer and HP 5970 Chemstation software.

The Y-tube olfactometer (Example 1) was used to assess the attractant activity of samples from various sources. Individual test results were analyzed by a $X^2$ test. The means and standard deviations were calculated for the replicates performed for each sample.

Figure 2:
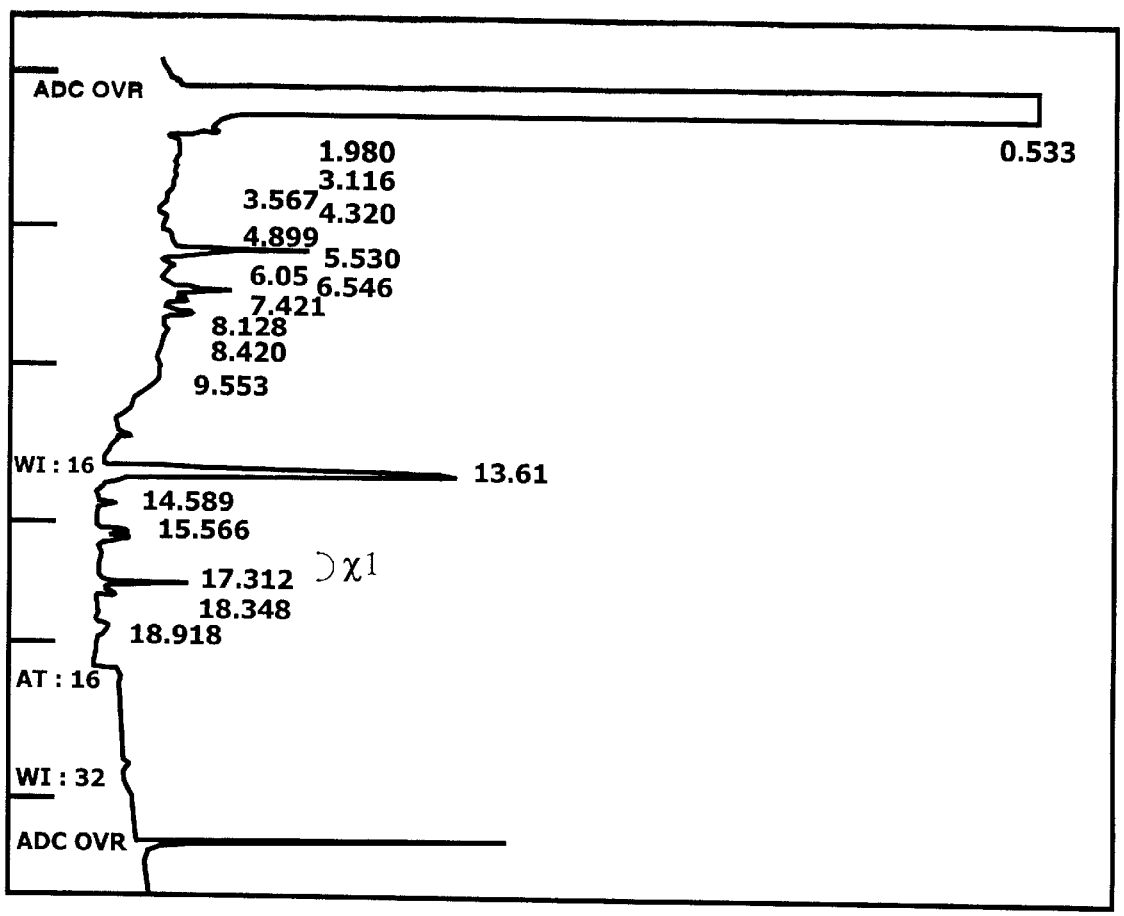
FIG. 2 is a gas chromatogram of soybean oil volatiles, where the effluent was split with one part going to the detector and ten parts diverted to a colony of ants. The DB-225 column was programmed from approximately 32° C. for about 10 minutes, then approximately 185° C. for about 10 minutes. The area marked active, induced worker clustering and rapid movement.
Figure 3A:
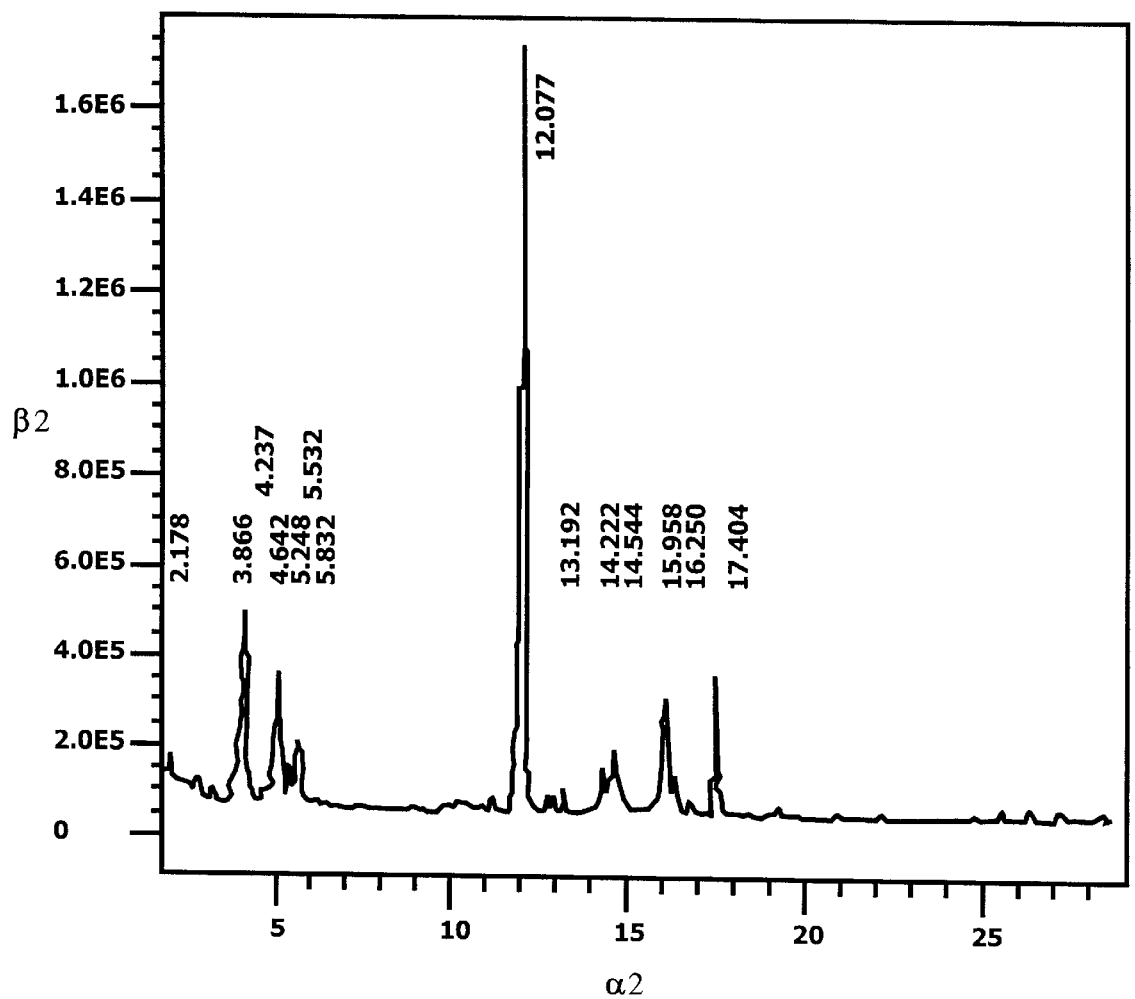
FIG. 3a is a total ion chromatograph. The DB-225 column was programmed from approximately 25° C. for about 10 minutes, then to approximately 185° C. for about 10 minutes.
Figure 3B:
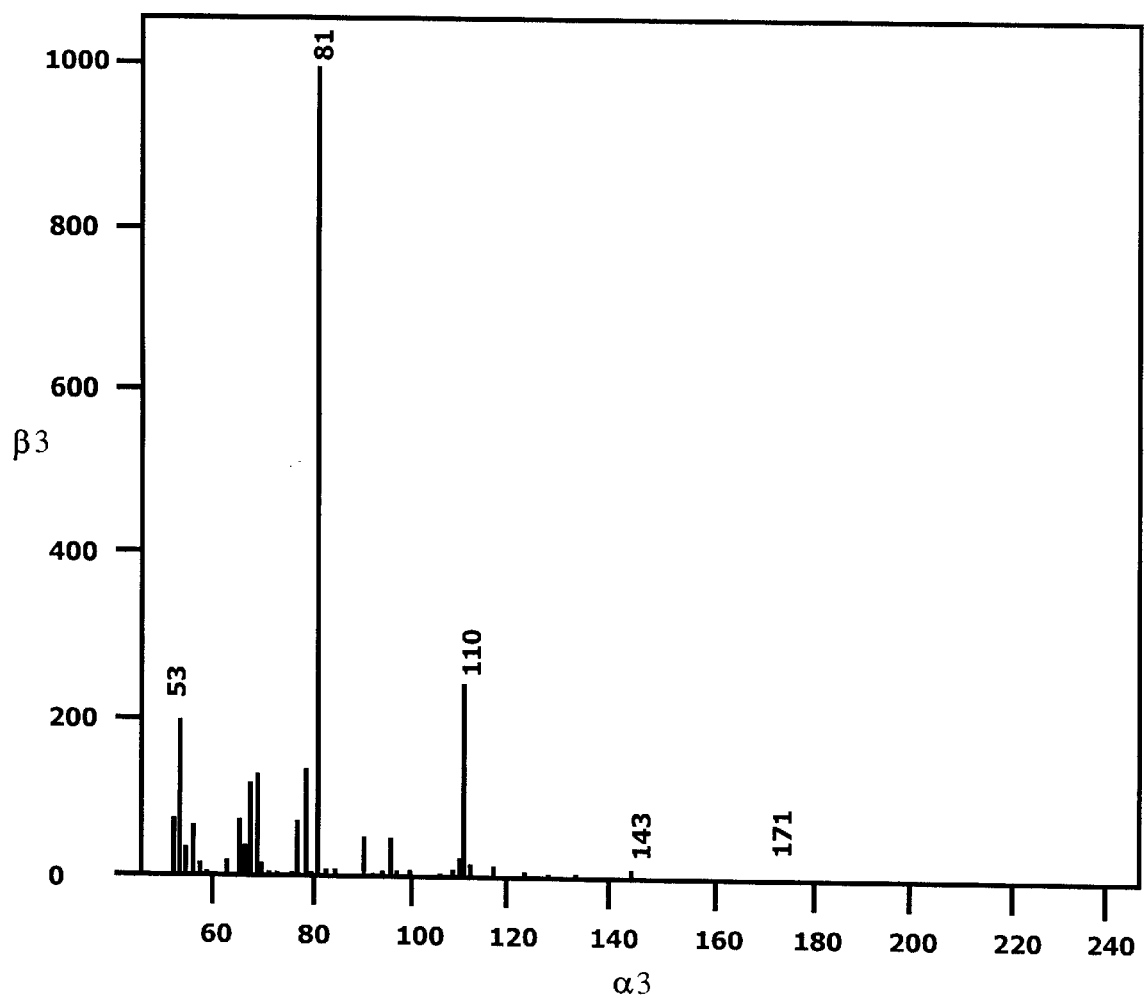
FIGS. 3b and 3c are EI mass spectra of the peaks in the active region of the chromatogram in FIG. 3a. The fragmentation pattern corresponds to isomers of 2,4-heptadienal (molecular weight=110).
Figure 3C:
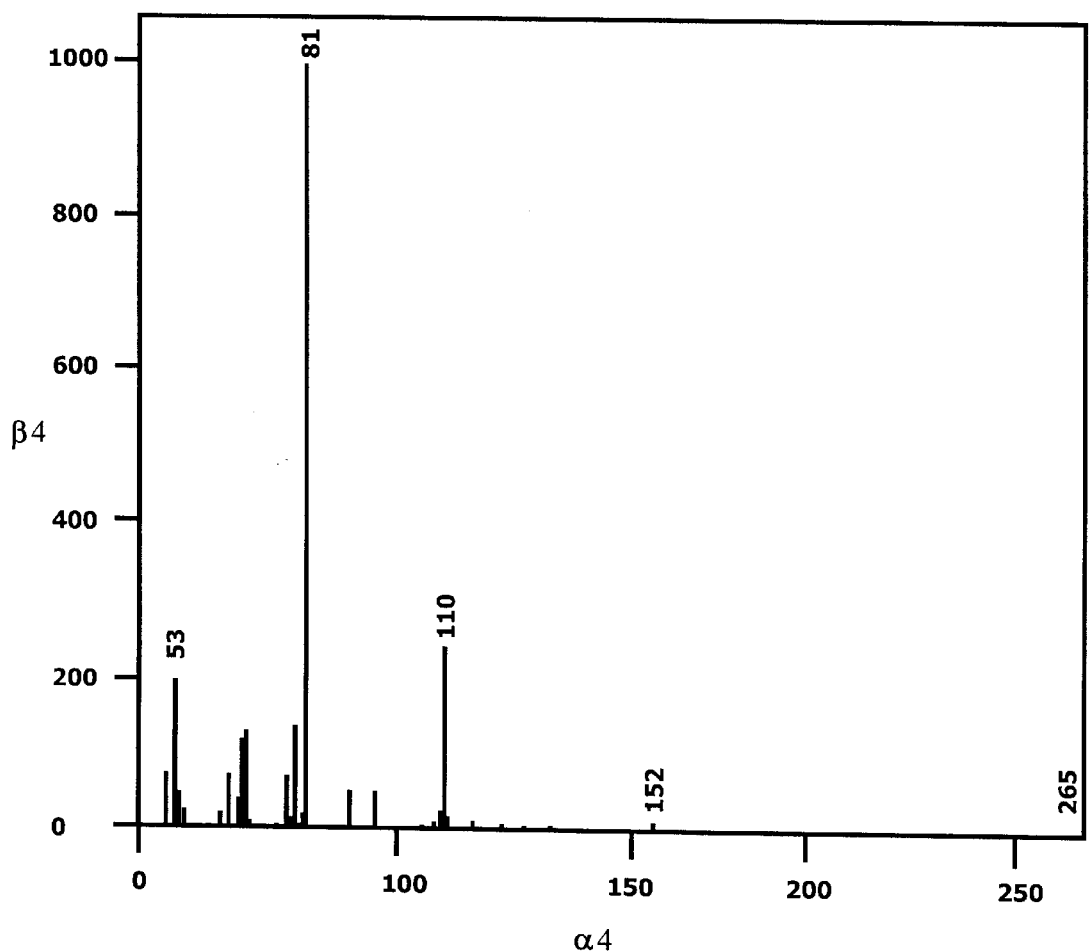
Figure 4A:
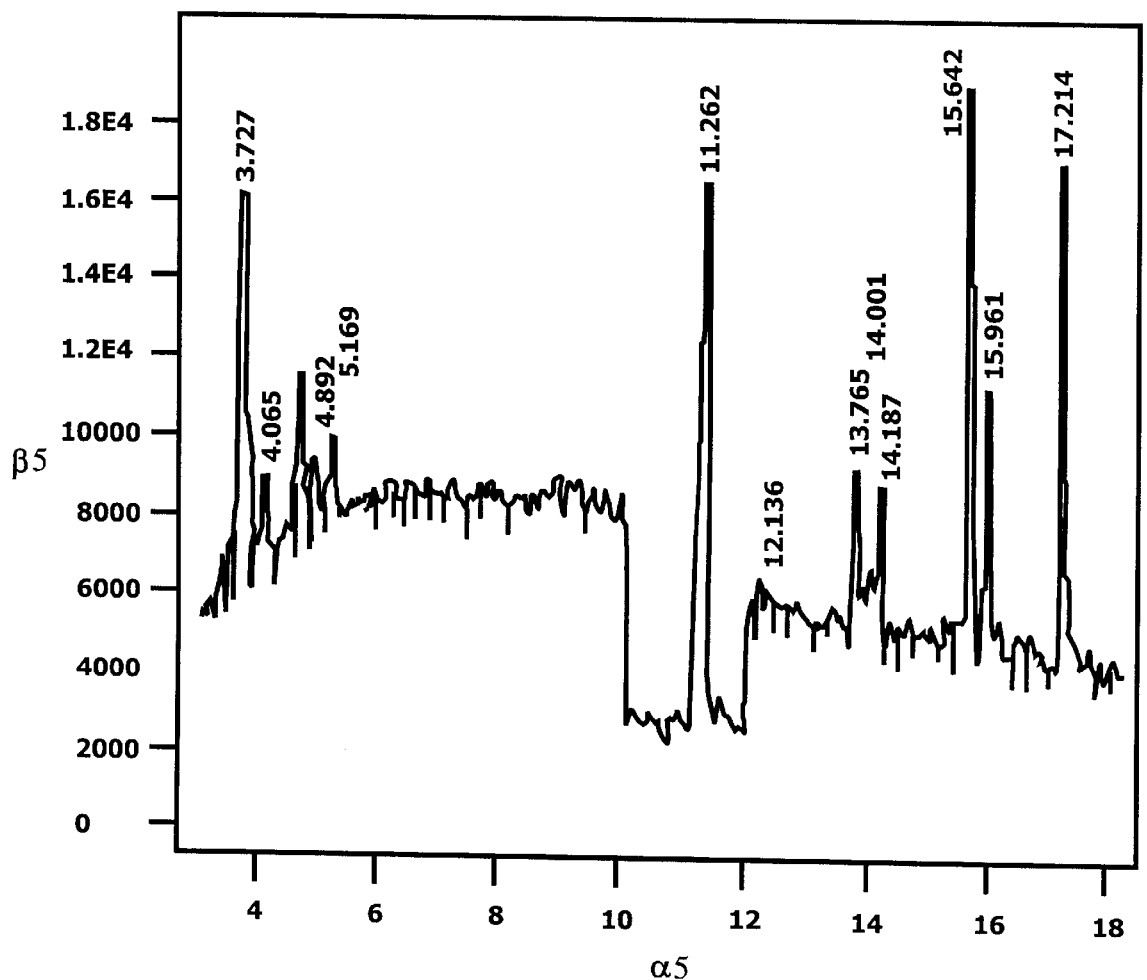
Figure 4B:
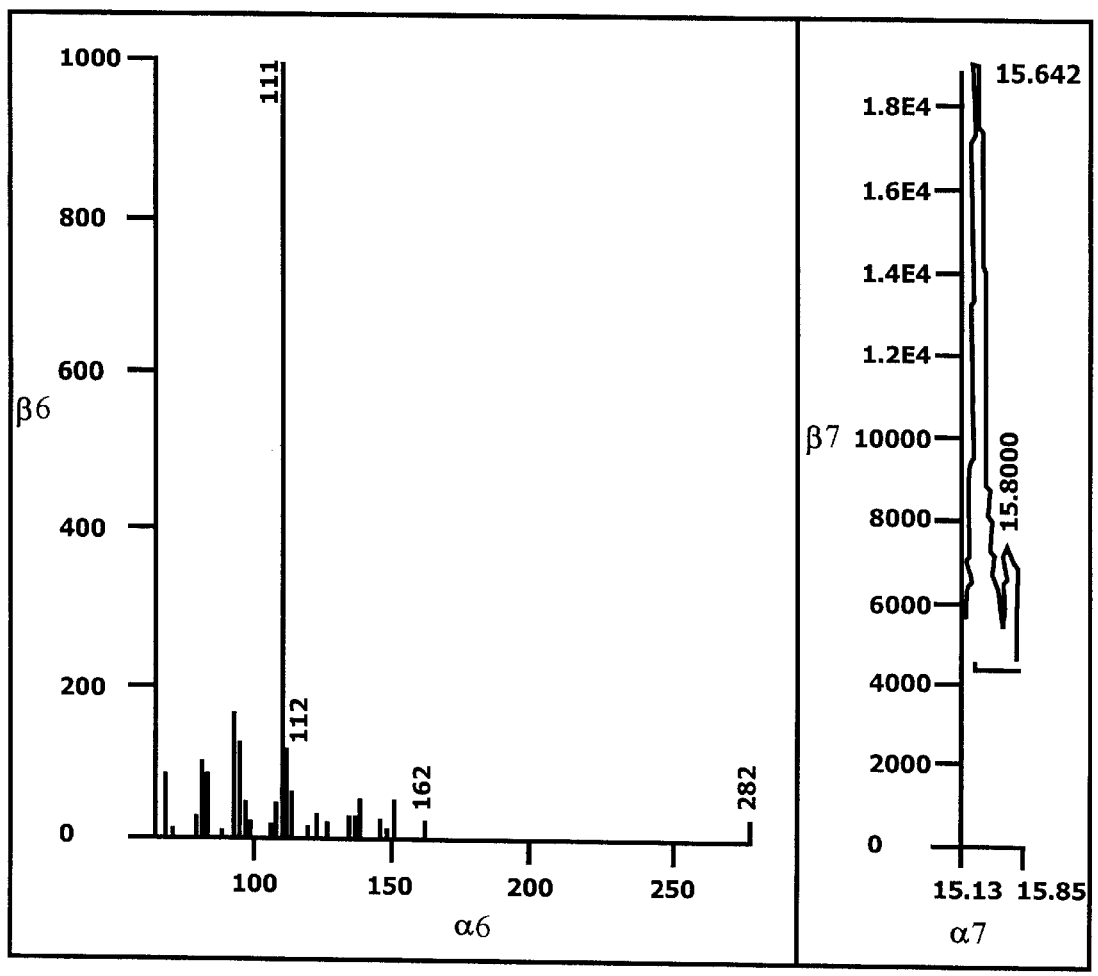
FIGS. 4b and 4c are CI mass spectra of the peaks in the active region of the chromatogram in FIG. 4a. M+1 is the base peak, indicative of a molecular weight of 110.
Figure 4C:
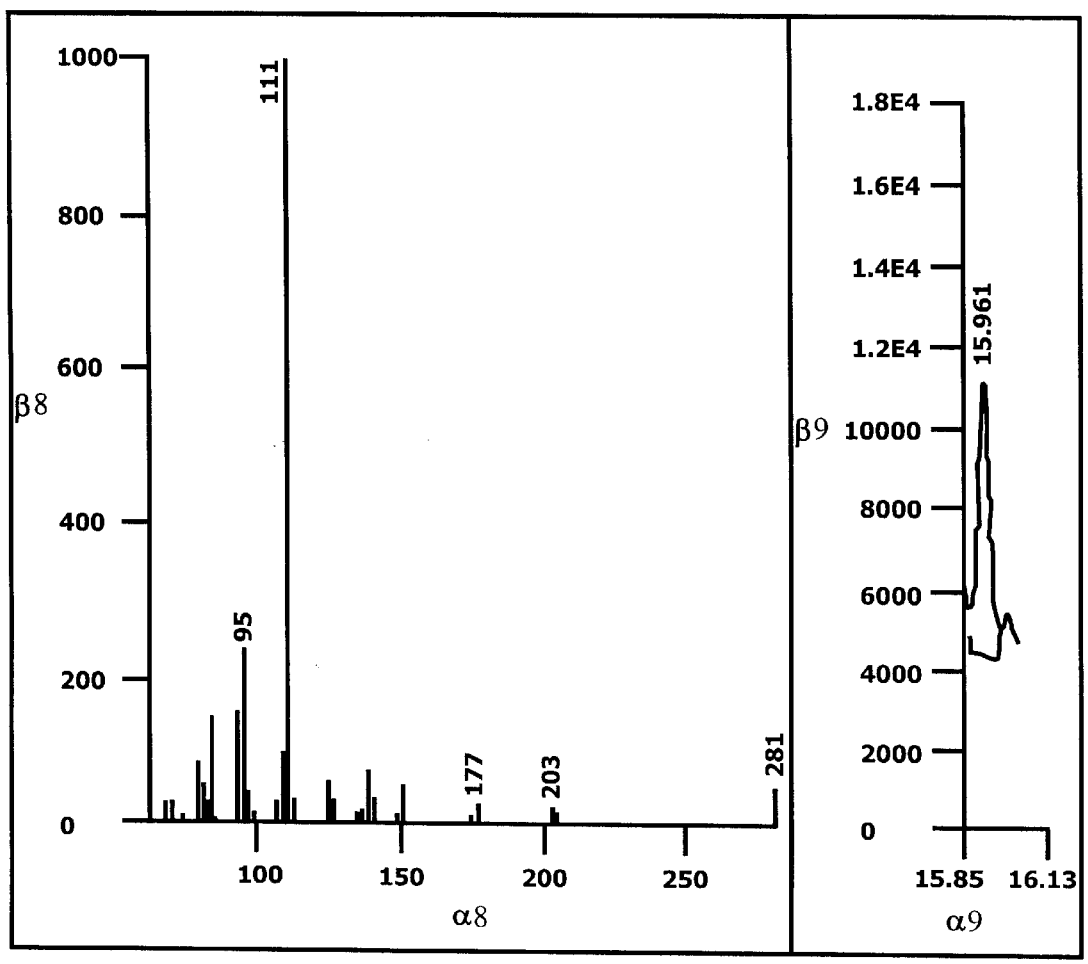

Preparative GC collection of the complex volatile mixture using a 10:1 splitter at the effluent end of the GC column (one part went to the detector and ten parts were directed to a capillary collection tube cooled with Dry-Ice) did not give good recovery due to the volatility of the compounds. To solve this, a worker ant activity bioassay was developed where the GC effluent was directed via a short length of TEFLON tubing to a small tray containing a fire ant subcolony. The column effluent was aimed at a worker food trail and the behavior of the ants monitored. When the ants detected an active compound they responded in an excited manner. The bioassay was replicated several times with similar results. The bioassays combined with the GC profiles showed the location of the active compounds in the gas chromatogram (FIG. 2). Combined gas chromatograph (GC) and mass spectrometry (MS) studies (EI and CI) enabled the determination of the basic chemical composition of the components in the soybean oil volatile mixture responsible for the ants' activity (FIGS. 3a–3c and 4a–4c). They were identified as 2,4-heptadienal isomers by their mass spectra and by comparison with authentic trans,trans-2,4-heptadienal, the only isomer commercially available (Aldrich Chemical Co.). Olfactometer bioassay of commercial trans,trans-2,4-heptadienal at the levels found in soybean oil volatiles showed it to be attractive to worker fire ants. Snyder et al (JAOCS, Vol. 65, No. 10, October 1988) quantified the volatile compounds from a variety of vegetable oils. They found that of the eight oils analyzed, only soybean oil and canola oil contained detectable amounts of trans,trans and trans,cis-2,4-heptadienal.

Figure 5:
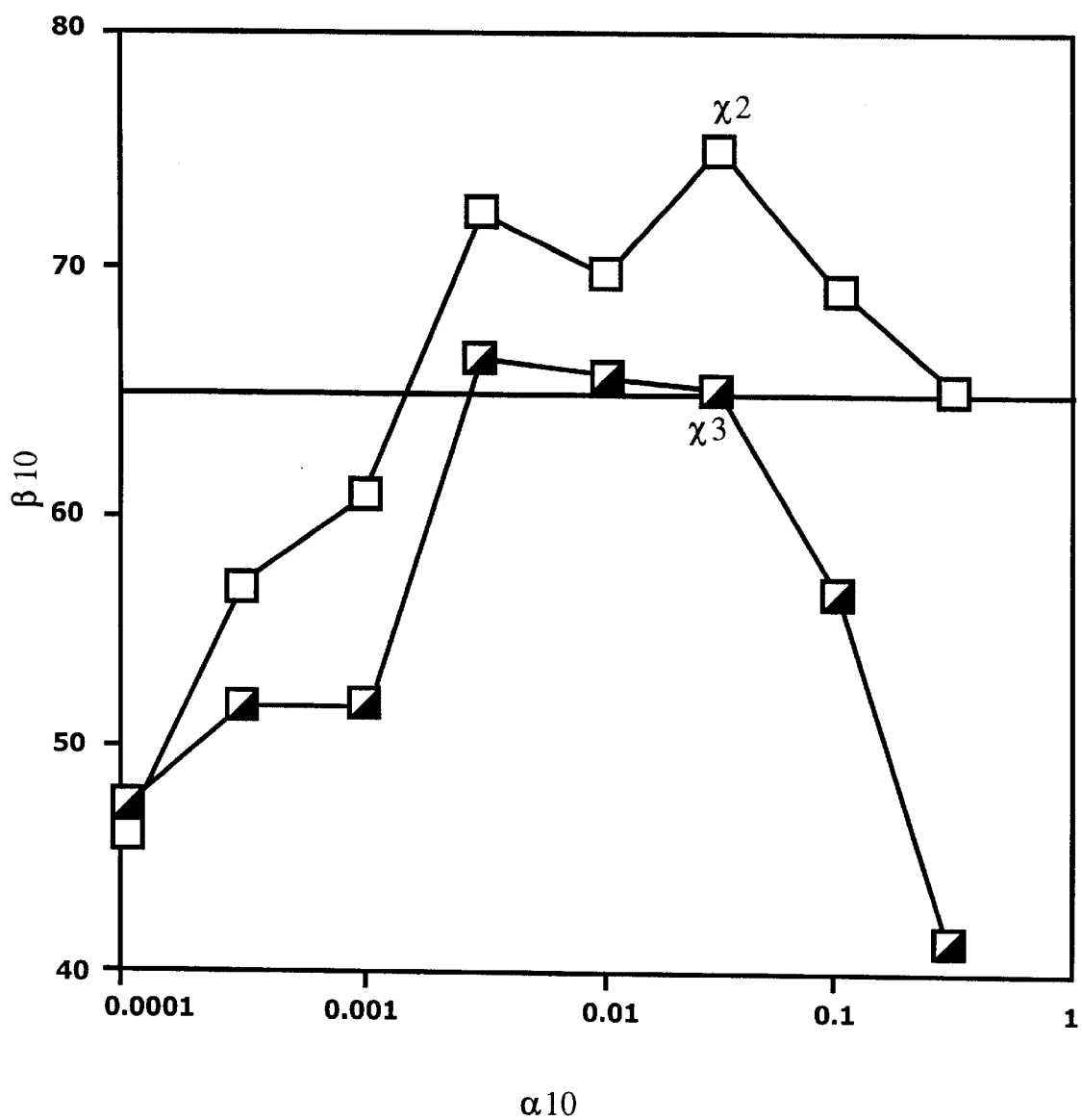
FIG. 5 is a graph showing comparison of the effect of concentration on worker activity (as measured in the olfactometer bioassay) for A) soybean oil volatiles and B) trans, trans-2,4-heptadienal. *=significantly attractive above this line.

The results of concentration/activity studies of soybean oil volatiles and equivalent concentrations of trans,trans-2,4-heptadienal are shown in FIG. 5. The two concentration curves are similar in shape but do not coincide. This is probably indicative of the additive effects of the two 2,4-heptadienal isomers.

EXAMPLE 4

Trans,trans-2,4-heptadienal (TTHD) was evaluated as an attractant for traps. The trap consisted of approximately 25 mm×65 mm plastic vials with lids. Four small holes were made just under the lids with a hot soldering iron. The inside surface of the vials was coated with FLUON® to prevent ants that entered the trap from getting out. Test material included once-refined soybean oil (ORSBO)containing TTHD at concentrations of about 0.01, 0.03 and 0.10% (weight:weight). The test material was placed on a piece of Whatman #1 filter paper that was cut to fit snugly inside the vial lid. A field site infested with fire ants was selected and the vials were randomly placed in the ground, such that the holes were at the soil surface. The number of ants trapped 6 and 24 hours after placement were recorded.

Each concentration was tested in 15 traps with 15 traps containing ORSBO alone, ORSBO with 0.01, 0.03, or 0.1% TTHD. The control was a blank with no oil or attractant. Three tests, in which traps were exposed for 6 hours and 24 hours were run. The results are shown below in Table 3. Generally more ants were caught in the traps containing ORSBO enhanced with TTHD than those with ORSBO alone. The data also show that a 24 hour trapping period was much better than 6 hours.

TABLE 3

| Total Number of Ants Trapped in indicated Test | | | |
|---|---|---|---|
| Attractant | 1 | 2 | 3 |
| 6 Hours | | | |
| Soybean Oil (SBO) | 22 | 73 | 118 |
| SBO + 0.01% TTHD | 17 | 73 | 77 |
| SBO + 0.03% TTHD | 25 | 146 | 114 |
| SBO + 0.1% TTHD | 51 | 207 | 141 |
| Blank | 5 | 19 | 21 |
| 24 Hours | | | |
| Soybean Oil | 43 | 145 | 138 |
| SBO + 0.01% TTHD | 281 | 171 | 219 |
| SBO + 0.03% TTHD | 215 | 128 | 349 |
| SBO + 0.1% TTHD | 278 | 323 | 348 |
| Blank | 19 | 41 | 85 |

EXAMPLE 5

Following the tests in Example 4 above, additional tests were run using about 0.1, 0.3 and 1.0% (weight:weight) to determine if higher concentrations would increase the number of ants trapped. Four tests were run using the same procedure described above in Example 4. The results are shown below in Table 4. Increasing the concentration of TTHD in ORSBO produced an increase in the number of ants trapped. In several of the tests those traps containing ORSBO with 0.3% TTHD caught fewer ants than those containing 0.01% TTHD. However, overall, the results indicate that TTHD increases the attractancy of the soybean oil.

TABLE 4

| Total Number of Ants Trapped in Indicated Test | | | | |
|---|---|---|---|---|
| ATTRACTANT | 1 | 2 | 3 | 4 |
| 6 Hours | | | | |
| Soybean Oil (SBO) | 89 | 130 | 127 | 116 |
| SBO + 0.1% TTHD | 240 | 170 | 135 | 210 |
| SBO + 0.3% TTHD | 115 | 87 | 100 | 187 |
| SBO + 1.0% TTHD | 145 | 132 | 280 | 317 |
| Blank | 25 | 22 | 17 | 15 |
| 24 Hours | | | | |
| Soybean Oil | 170 | 219 | 332 | 413 |
| SBO + 0.1% TTHD | 219 | 219 | 381 | 560 |
| SBO + 0.3% TTHD | 349 | 239 | 359 | 427 |
| SBO + 1.0% TTHD | 348 | 182 | 403 | 707 |
| Blank | 85 | 36 | 59 | 38 |

EXAMPLE 6

Figure 6:
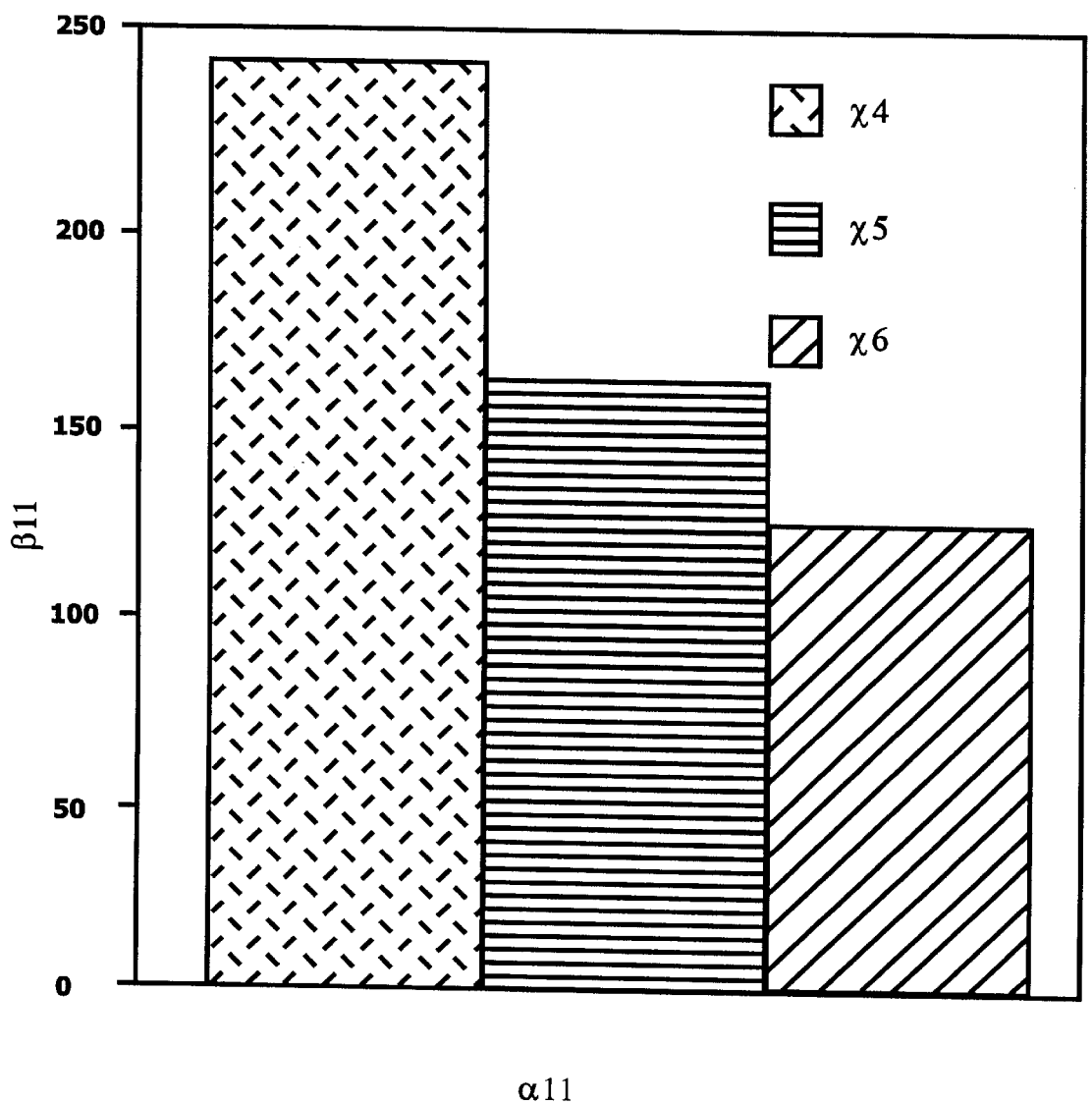
FIG. 6 is a graph showing enhanced fire ant trap catches for the indicated vegetable oil, when soybean oil volatiles were added to each oil. 100% means there was no enhancement of trap catches. For peanut and soybean oil N=18. For olive oil N=6.

Attractant soybean oil volatiles were added to peanut and olive oils which are not attractive to fire ants (See Example 1, Table 1 above). A point source bioassay was conducted (Vander Meer et al., J. Chem. Ecol., Volume 14, 825–838, 1988; herein incorporated by reference). One or two cells from each laboratory reared S. invicta colony were placed on top of each other in the center of a plastic tray (7×44×56 cm). Ten positions were symmetrically marked around a 20 cm radius from the tray's center. The ants were allowed a minimum of 1 hr to acclimate to their new surroundings. Blotter paper squares (2×2 cm) marked with 1.5 cm diameter circles were placed on slightly larger squares of aluminum foil. Samples to be tested were randomly placed on the numbered positions. Approximately 99 μl of peanut, olive or soybean oil containing approximately 1 μl attractant soybean oil volatiles, collected as described in Example 4, were applied to the paper squares. The samples induced worker ants to aggregate and feed at the material on the blotter paper squares. The number of ants within the 1.5 cm circle were counted at 5 min intervals for 30 min. The result for each location was the sum of the six counts. Each test was replicated on different *S. invicta* colonies. In order to minimize colony variation the results for each replicate were converted to a percent response by finding the sum of all ants responding and dividing this into the result for each treatment. This result was multiplied by 100 to obtain a percent. The average percent response for the indicated number of replicates is shown in FIG. 6. One hundred percent means there was no enhancement of the vegetable oil. For peanut and soybean oil N=18. For olive oil N=6. The results show that vegetable oils which have no attractive properties become attractive when attractant soybean oil volatiles are added.

EXAMPLE 7

Trans,trans-2,4-heptadienal was added to a Nylar bait formulation to test if it enhances the bait using the olfactometer bioassay described above in Example 1. The active ingredient, Nylar, is an insect growth regulator which regulates the reproductive systems of the queen. In addition, brood present at the time of treatment may develop into sexual forms rather than workers. The colonies die through worker attrition in that replacement workers are not produced. The entire process may require several months.

Any result that had 65% or greater of the ants attracted to the sample side of the olfactometer is a statistically significant attractant. The formulations tested were approximately 0.5% Nylar in approximately 30% soybean oil (final product percentages) absorbed onto distillers grain (DG) or pregel defatted corn grits as control. The test samples had approximately 0.005% trans,trans-2,4-heptadienal.

Figure 7:
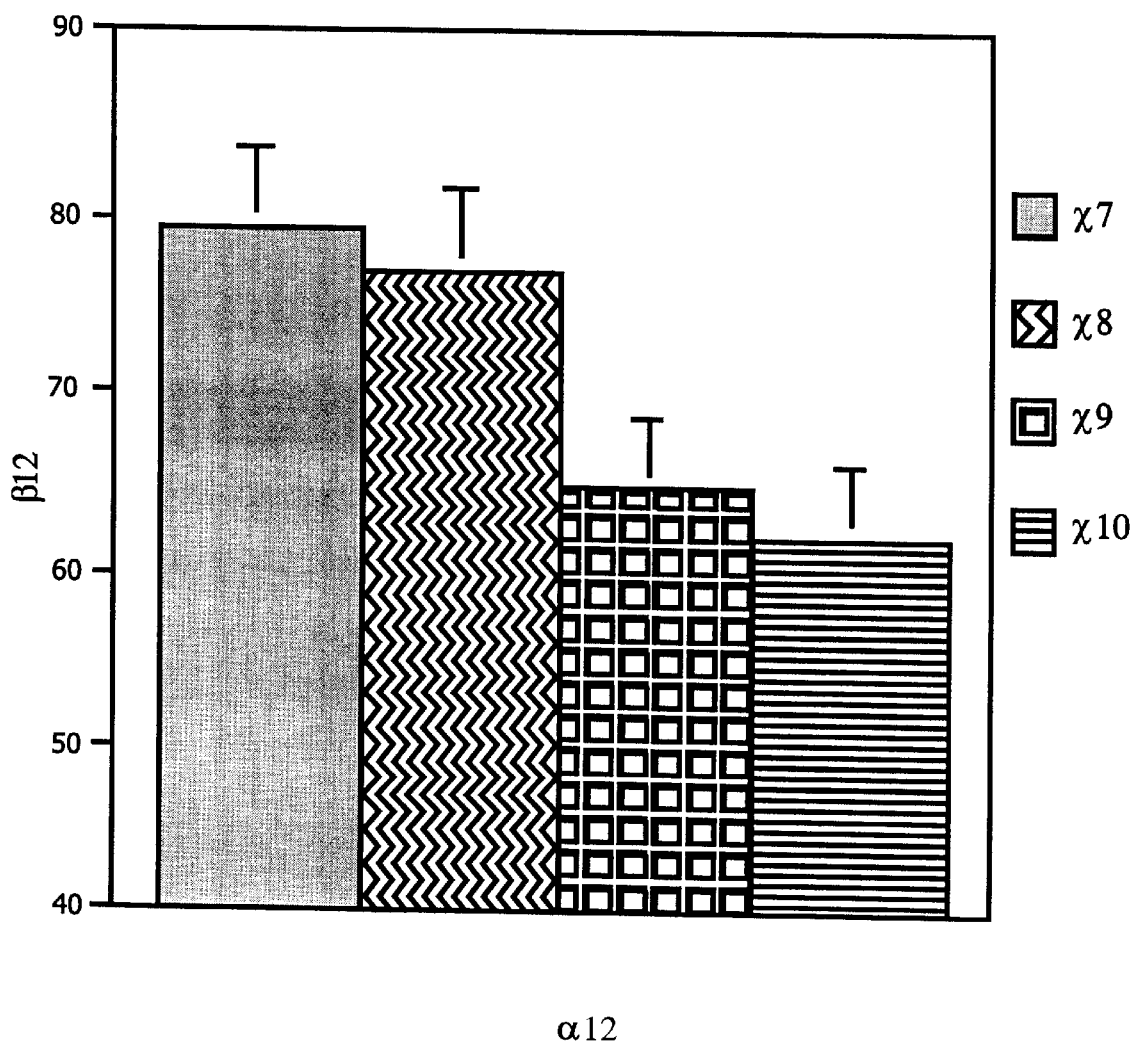
FIG. 7 is a graph showing olfactometer results for baits with and without trans,trans-2,4-heptadienal.

The results are shown in FIG. 7. The incorporation of trans,trans-2,4-heptadienal to either carrier gave a higher mean value and a tighter standard error. This means the results were more consistent with the 2,4-heptadienal attractant added.

EXAMPLE 8

Nylar containing baits with and without trans,trans-2,4-heptadienal were tested under field conditions. The test site was a pasture with grazing cattle. The type of fire ant population present (monogyne versus polygyne) was determined by aggression assays (Morel et al, Ann. Entomol. Soc. Am., Volume 83, 642–647, 1990; herein incorporated by reference). Mixed monogyne and polygyne fields and fields where populations of *Solenopsis invicta* and *S. geminata* were found together were not used.

The population index of each colony in the study site was estimated by digging up a portion of the mound. Mound depth, size and ant density were all recorded as were the qualitative variables such as the presence and absence of worker brood, the presence and absence of sexual brood or alates and the general shape of the mound. This information was used to calculate a mound's Population Index (PI; Table 5 below). Mounds were segregated based on their PI and proximity to each other. Each set of replicates for each treatment were matched based on the PI of the test mounds.

The bait treatments were composed of a standard, Amdro (the carrier is pregel defatted corn cob grits, PDCG); approximately 0.5% Nylar in soybean oil on distillers grain; and approximately 0.5% Nylar plus approximately 0.005% trans,trans-2,4-heptadienal in soybean oil on distillers grain. The control was untreated. The Amdro standard was broadcast over about a 50×50 foot area using an All Terrain Vehicle (ATV) equipped with a Herd spreader. The application rate was about 1–1.5 pounds per acre. Both Nylar containing formulations were put out at a rate of about 12 grams per mound. A scoop was used to distribute the bait to the three locations immediately around the target.

Mounds were checked at regular intervals after application to look for changes in the PI. Generally, evaluations were made after about 3,6,9 and 12 weeks post treatment. PI determinations were made without knowledge of the treatment used. Each mound was considered separately during the evaluation process (the rank of one mound in a pair was not linked with the other) and PI readings were independent of their previous reading. The data were checked afterwards for any gross inconsistencies with previous evaluations. This was necessary because fire ant colonies will change location for a variety of reasons including physical disturbance and environmental changes such as temperature, rainfall, decreased competition from other colonies, etc. Generally, four to five matched replicates were set up per experiment.

Figure 8:
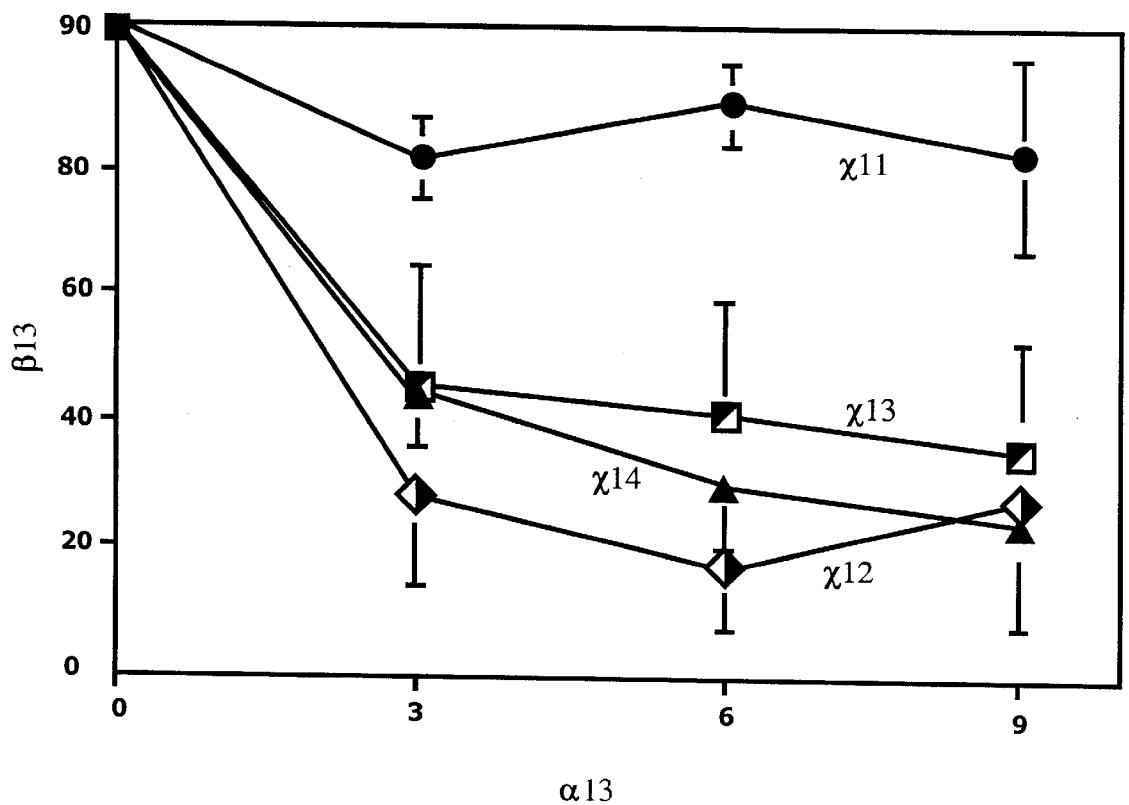
FIG. 8 is a graph showing single mound treatments of monogyne *Solenopsis invicta* colonies in the field. The mean and standard error are reported for four-five replicates.

The results are shown in FIG. 8. As expected, Amdro (a toxicant) showed more rapid activity then the Nylar (insect growth regulator) treatments. However, by nine weeks there was little difference in the mean population rank of the two Nylar treatments and the Amdro standard. Although there is probably not a significant difference between Nylar and Nylar+trans,trans-2,4-heptadienal, the mean value for the attractant enhanced bait containing Nylar is lower than the non-enhanced Nylar. Therefore, the Nylar containing bait with approximately 0.005% trans,trans-2,4-heptadienal works better than the bait with no attractant.

TABLE 5

| NUMBER OF WORKERS | NUMERICAL RANKING |
|---|---|
| Less than 1,000 Ants | 0 |
| 1,000 to 10,000 Ants | 10 with brood 20 |
| 10,000 to 50,000 Ants | 20 with brood 40 |
| 50,000 to 100,000 Ants | 30 with brood 60 |
| 100,000 to 150,000 Ants | 40 with brood 80 |
| 150,000+ Ants | 50 with brood 100 |

EXAMPLE 9

Nylar baits with and without trans,trans-2,4-heptadienal were tested under home owner conditions. The treatments were approximately 0.5% Nylar in soybean oil and on distillers grain; and approximately 0.5% Nylar plus approximately 0.005% trans,trans-2,4-heptadienal in soybean oil and on distillers grain. The control was untreated. The Nylar treatments were prepared and separated into about 36 gram units kept in a beaker covered with aluminum foil. Twelve mounds were chosen based on location and size (a ranking of at least 40 PI; Table 5 above). From these 12 mounds, four were picked at random for each of the treatments. Three aliquots of approximately 4 grams each were placed around the periphery of each mound for a total of approximately 12 grams/mound. The amount of bait was estimated based from the 36 gram beaker to simulate homeowner conditions where a homeowner will have a packet containing enough bait to treat three mounds.

Figure 9:
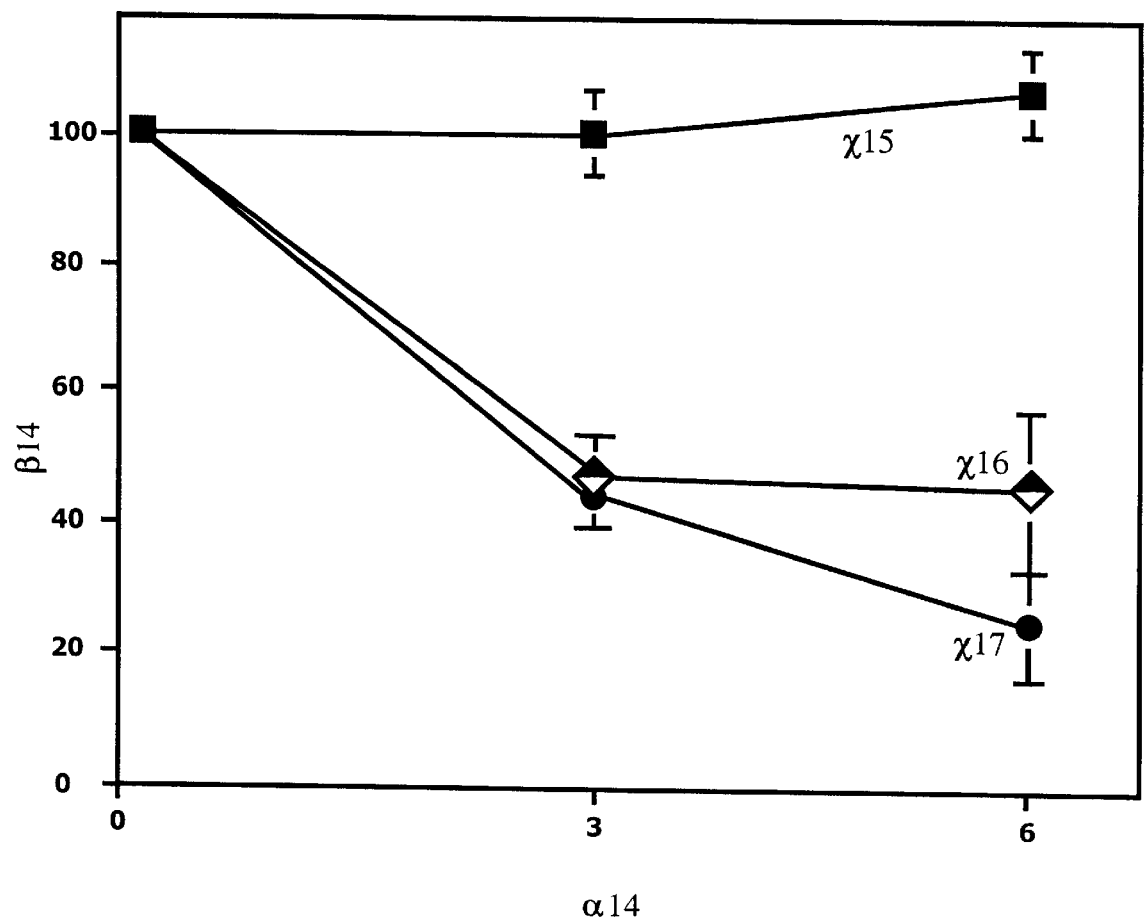
FIG. 9 is a graph showing mound treatments under urban field conditions of monogyne Solenopsis invicta. The mean and standard error are reported for four replicates.

The results are shown in FIG. 9. Only six weeks of data were available. The bait containing the trans,trans-2,4-heptadienal showed a greater reduction in the population index compared to the bait without the attractant. This is supportive evidence for the trend shown in FIG. 8, Example 7, where the Nylar+attractant also had a lower mean value. Although brood is present in some of the replicates, it is sexual brood, as expected from the treatment with Nylar which is an insect growth regulator.

The foregoing detailed description is for the purpose of illustration. Others skilled in the art can apply the knowledge described to other baits and for the control of other social insect pests. Such detail is solely for that purpose and those skilled in the art can make variations therein without departing from the spirit and scope of the invention.

INDEX OF THE ELEMENTS

1. Air Inlet Tube
2. Sample Chamber
3. Baffle
4. Ring Seal Tube (Front)
5. Ring Seal Tube (Rear)
6. Entrance Stem
7. Ring
8. Arms
9. Y-Tube

We claim:

1. A composition for attracting social pest insects comprising a pest insect attracting amount of 2,4-heptadienal, and a carrier material.

2. The composition of claim 1 wherein the 2,4-heptadienal is trans,trans-2,4-heptadienal, trans,cis-2,4-heptadienal and mixtures thereof.

3. A method for attracting social pest insects to a bait or a trap comprising
treating an object or area with a social pest insect attracting amount of a composition of claim 1.

4. A method for attracting social pest insects to a bait or a trap comprising
treating an object or area with an a social pest insect attracting amount of the composition of claim 1.

5. The method of claim 4 wherein the 2,4-heptadienal is trans,trans-2,4-heptadienal, trans,cis-2,4-heptadienal and mixtures thereof.

6. A composition for attracting social pest insects consisting essentially of
a pest insect attracting volatile from soybean oil or canola oil, and
a carrier material.

7. A composition for attracting social pest insects comprising
a pest insect attracting volatile from canola oil, and
a carrier material.

8. A composition for attracting social pest insects comprising
a pest insect attracting volatile from soybean oil or canola oil wherein said volatile is in a concentration of about 0.001% to about 2% by weight, and
a carrier material.

9. The composition of claim 6 wherein said volatile is in a concentration of about 0.003% to about 0.03% by weight.

* * * * *